(12) United States Patent
Peyman et al.

(10) Patent No.: US 8,430,862 B2
(45) Date of Patent: *Apr. 30, 2013

(54) SUBCONJUNCTIVAL AGENT DELIVERY APPARATUS, SYSTEM AND METHOD

(75) Inventors: Gholam A. Peyman, Sun City, AZ (US); Michel Jean Noel Cormier, Mountain View, CA (US); Kamran Hosseini, Hayward, CA (US)

(73) Assignee: KMG Pharma LLC, Mountain View, CA (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/932,941

(22) Filed: Mar. 9, 2011

(65) Prior Publication Data

US 2011/0251586 A1    Oct. 13, 2011

Related U.S. Application Data

(60) Provisional application No. 61/342,157, filed on Apr. 8, 2010.

(51) Int. Cl.
*A61H 33/04*    (2006.01)
*A61M 31/00*    (2006.01)

(52) U.S. Cl.
USPC .......................................... 604/521; 604/301

(58) Field of Classification Search .......... 604/300–302, 604/116, 506, 521
See application file for complete search history.

(56) References Cited

U.S. PATENT DOCUMENTS

| | | | |
|---|---|---|---|
| 6,309,374 B1 * | 10/2001 | Hecker et al. | 604/117 |
| 6,746,429 B2 | 6/2004 | Sadowski et al. | |
| 7,678,078 B1 | 3/2010 | Peyman et al. | |
| 2003/0229308 A1 * | 12/2003 | Tsals et al. | 604/116 |
| 2007/0055200 A1 | 3/2007 | Gilbert | |
| 2007/0055214 A1 * | 3/2007 | Gilbert | 604/500 |
| 2007/0260210 A1 | 11/2007 | Conroy | |
| 2008/0058760 A1 * | 3/2008 | Agerup | 604/521 |
| 2009/0018602 A1 * | 1/2009 | Mitelberg et al. | 607/40 |

* cited by examiner

*Primary Examiner* — Kevin C Sirmons
*Assistant Examiner* — Bradley Osinski
(74) *Attorney, Agent, or Firm* — Francis Law Group

(57) ABSTRACT

A subconjunctival injection apparatus for administering a pharmacological agent formulation to a subconjunctival compartment of an eye, the apparatus including a jet injector having force generating means that is adapted to generate sufficient force to expel the pharmacological agent formulation from the jet injector and through the conjunctiva. In one embodiment of the invention, the jet injector comprises a needleless jet injector. In one embodiment, the needleless jet injector provides a delivery pressure in the range of approximately 100-1000 psi.

4 Claims, 4 Drawing Sheets

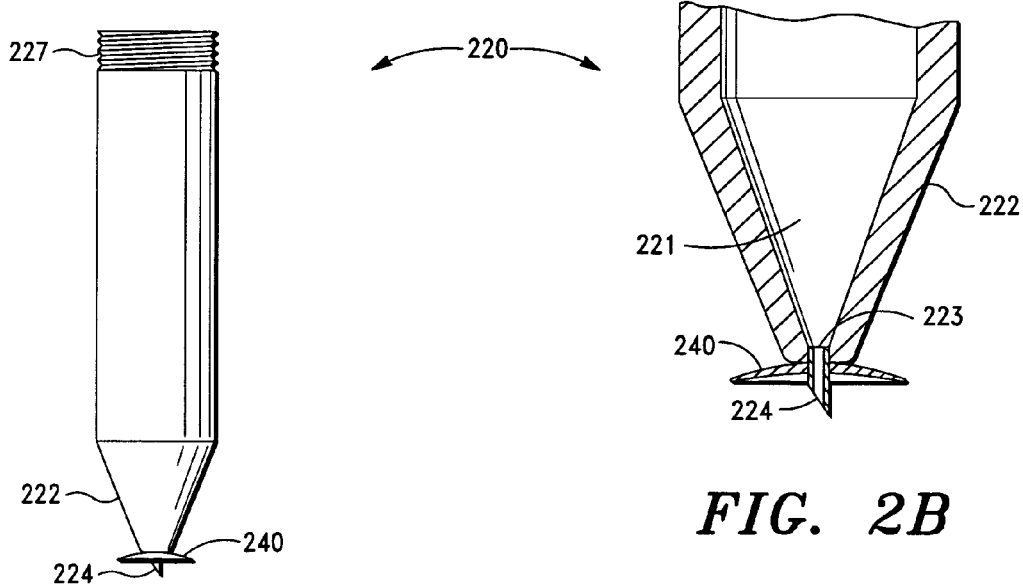
FIG. 2A
FIG. 2B
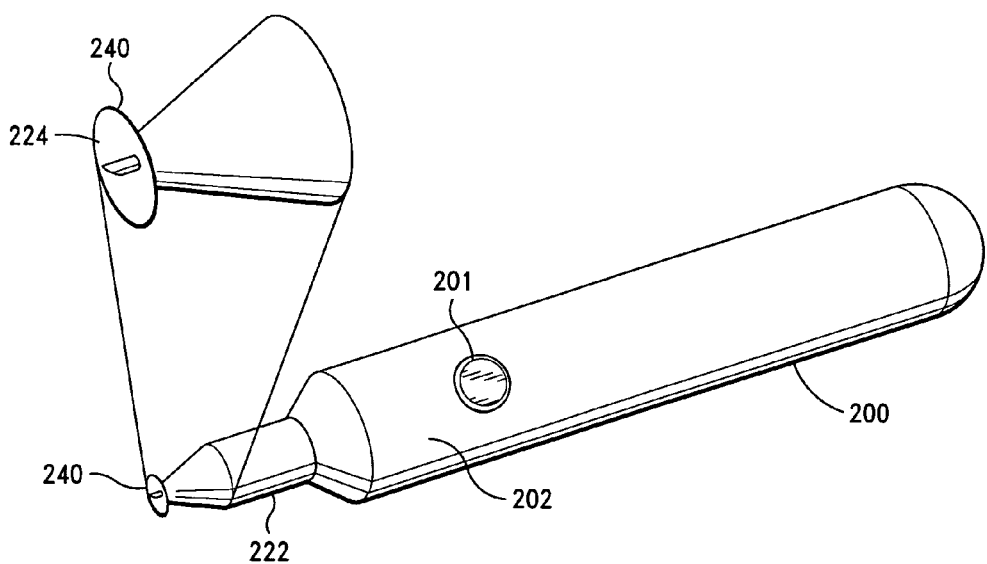
FIG. 2C

FIG. 4A  FIG. 4B

SUBCONJUNCTIVAL AGENT DELIVERY APPARATUS, SYSTEM AND METHOD

CROSS-REFERENCE TO RELATED APPLICATIONS

This application claims the benefit of U.S. Provisional Application No. 61/342,157, filed Apr. 8, 2010.

FIELD OF THE INVENTION

This invention relates generally to subconjunctival agent delivery or administration as a means of treating various conditions of the eye. More particularly, the invention relates to improved means for performing a subconjunctival agent delivery with the benefits of improved safety for the patient and increased efficiency for the practitioner.

BACKGROUND OF THE INVENTION

As is well known in the art, delivery of pharmacological agents (or drugs) to a specific organ or tissue can be achieved through systemic or local administration. In systemic administration, the agent is introduced into the systemic, or general, circulation by ingestion, injection, inhalation or transdermal administration. Circulating blood delivers the agent to the target tissue by either passive or active transport.

Advantages of systemic administration are that this mode of administration, especially by ingestion, is simple and well accepted by the patient. A disadvantage, however, is that the agent must be administered at relatively high doses in order to reach the target area in sufficient quantity. Moreover, the agent is delivered to the entire body, which can include sites where the agent can cause significant side effects. This is especially true for chemotherapeutic agents that tend to present significant systemic toxicity, and steroids, which present significant long-term systemic side effects.

Another significant disadvantage of systemic administration is that transfer of many pharmacological agents from the blood to certain tissues, such as the brain or an eye, is very inefficient.

An alternative to systemic administration is to administer the pharmacological agent(s) into a target organ (or tissue) or in close proximity thereto. However, as is well known in the art, local administration of an agent into or proximate an organ, particularly, an eye, typically requires strict adherence to numerous safeguards.

As discussed in detail herein, the eye is a delicate sense organ that is surrounded by specialized structures and protected by the orbit bones, soft tissues and eyelids. The eye itself is composed of three primary layers: the sclera, the uvea, and the retina. The iris, ciliary body and choroid constitute the uvea.

Because of the complex nature of the eye, it is susceptible to a large number of abnormalities (and/or diseases). The abnormalities include dry eye, allergies, infections, various inflammatory diseases and glaucoma.

Treatments of the abnormalities and diseases have, in general, been limited to topical administration of agents or preparations. A conventional example of topical administration of an agent to the eye is the delivery of timolol via eye drops.

As is well known in the art, eye drops facilitate transmission of the agent directly to the anterior part of the eye by instillation into the cul-de-sac. The agents are then moved via the tears of the eye across the cornea and sclera into the anterior and posterior chambers of the eye without initially entering the systemic circulation path.

The advantage of this mode of administration (or delivery) is that the agent is concentrated in the target tissue with a much lower systemic exposure. This tends to reduce the above-mentioned systemic effects.

A disadvantage of this mode of administration is that not all eye tissues are accessible by this route of delivery. Tears can also redirect a significant portion of the agent away from the target area relatively quickly.

A further disadvantage of this mode of administration is that it is mostly applicable to small molecular weight pharmacological agents. Indeed, large molecular weight agents, such as antibodies, are known to diffuse poorly across the conjunctiva.

As is well known in the art, subconjunctival delivery of therapeutic agents is currently performed using a conventional needle and syringe, i.e. subconjunctival injection. As is also well known in the art, this method requires highly skilled and trained personnel and present many risk associated with it. Risks include needle injury to the patient and the practitioner, as well as risks associated with disposal of the needle.

Recently, intraocular injection using needleless jet injection has been employed to administer agents to the eye. Illustrative are the methods and systems disclosed in U.S. Pat. Pub. Nos. 2004/0210188, 2007/0052139, 2007/0055199, 2007/0055200, 2007/0055214, 20090118738, WO2007058966. However, the disclosed method and systems are only compatible with deep intravitreal injection and do not include injection in the outermost layers of the eye, particularly subconjunctival injection. A major disadvantage is that the high pressures involved for the liquid jet to go through the outer membrane of the eye and into the vitreous compartment is the associated risk of retinal detachment.

Associated with the development of new pharmacological treatments for ocular diseases, specialists are being faced with the responsibility for meeting the ever increasing demand for subconjunctival administration of pharmacological agents and, hence, addressing the aforementioned issues associated with the prior art subcutaneous injection methods and systems. There is also no universally accepted standard process for performing a subconjunctival injection.

Further, subconjunctival injections cannot always be scheduled in advance and each injection requires several steps to prepare the eye and safely perform the injection. The time required to perform injections can thus disrupt office schedules, resulting in unexpected prolongation of patient waiting times.

Therefore, a method and device to standardize and simplify the subconjunctival agent delivery process, improve patient comfort and safety, and increase efficiency of the process is desired.

It is therefore an object of the present invention to provide a subconjunctival agent delivery method and system that provides safe, accurate, consistent, and rapid delivery of therapeutic agents into the subconjunctival space or compartment of the eye.

It is another object of the present invention to provide a subconjunctival agent delivery method and system that facilitates delivery of therapeutic agents into the subconjunctival compartment of the eye with minimal risk of trauma to the patient's eye by the delivery system.

It is another object of the present invention to provide a subconjunctival agent delivery method and system that facilitates delivery of therapeutic agents into the subconjunctival, subtenon spaces or intrascleral and subchoroidal space of the eye.

It is another object of the present invention to provide a subconjunctival agent delivery method and system that facilitates delivery of therapeutic agents into the subconjunctival compartment of the eye with minimal risk of trauma and infection.

It is another object of the present invention to provide a subconjunctival agent delivery method and system that provides semi-automated delivery of therapeutic agents into the subconjunctival compartment of the eye.

SUMMARY OF THE INVENTION

In accordance with the above objects and those that will be mentioned and will become apparent below, in one embodiment of the invention, there is disclosed a subconjunctival agent delivery apparatus for administering a pharmacological agent formulation to a subconjunctival compartment of an eye, comprising injector means having force generating means that is adapted to generate sufficient force to expel the pharmacological agent formulation from the injector means and into and through the conjunctiva.

In one embodiment of the invention, the injector means comprises a needleless jet injector.

In one embodiment of the invention, the injector means comprises a microneedle jet injector.

In one embodiment of the invention, the injector means provides a delivery pressure in the range of approximately 100-1000 psi.

In one embodiment of the invention, the volume of the pharmacological agent formulation administered to the eye is in the range of approximately 0.025-1 ml.

In one embodiment of the invention, the injector means includes a positioning platform for positioning the injector means on an eye structure In a preferred embodiment of the invention, the eye structure comprises the conjunctiva.

In some embodiments of the invention, the positioning platform has a substantially circular shape.

In a preferred embodiment of the invention, the positioning platform has an eye contact surface that substantially conforms to the surface of the sclera of an eye.

In one embodiment of the invention, the platform includes suction means, such as those disclosed in Applicants' issued U.S. Pat. No. 7,678,078. As set forth in the noted patent, the suction means provides an engagement force when the platform is positioned on the eye. Examples of suitable suction means include, without limitation, suction cups and suction rings.

In accordance with another embodiment of the invention, there is disclosed a method for administering a pharmacological agent formulation to a subconjunctival compartment of an eye, comprising the steps of (i) providing a subconjunctival agent delivery apparatus having the pharmacological agent formulation contained in an internal formulation chamber, (ii) positioning the subconjunctival agent delivery apparatus on the conjunctiva of the eye, and (iv) activating the agent delivery apparatus, whereby the pharmacological agent formulation is expelled from the agent delivery apparatus and into the subconjunctival compartment of the eye.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 2A is a front plane view of a microneedle jet injector transfer mechanism, in accordance with one embodiment of the invention;

FIG. 2B is a partial sectional front plane view of the microneedle jet injector transfer mechanism shown in FIG. 2A, in accordance with one embodiment of the invention;

FIG. 2C is a perspective view of a microneedle jet injector having the microneedle jet injector transfer mechanism shown in FIG. 2A, in accordance with one embodiment of the invention;

FIGS. 4A and 4B are plane views of an assembled needleless jet injector positioned on an eye, in accordance with one embodiment of the invention.

DETAILED DESCRIPTION OF THE PREFERRED EMBODIMENTS

Figure 1:
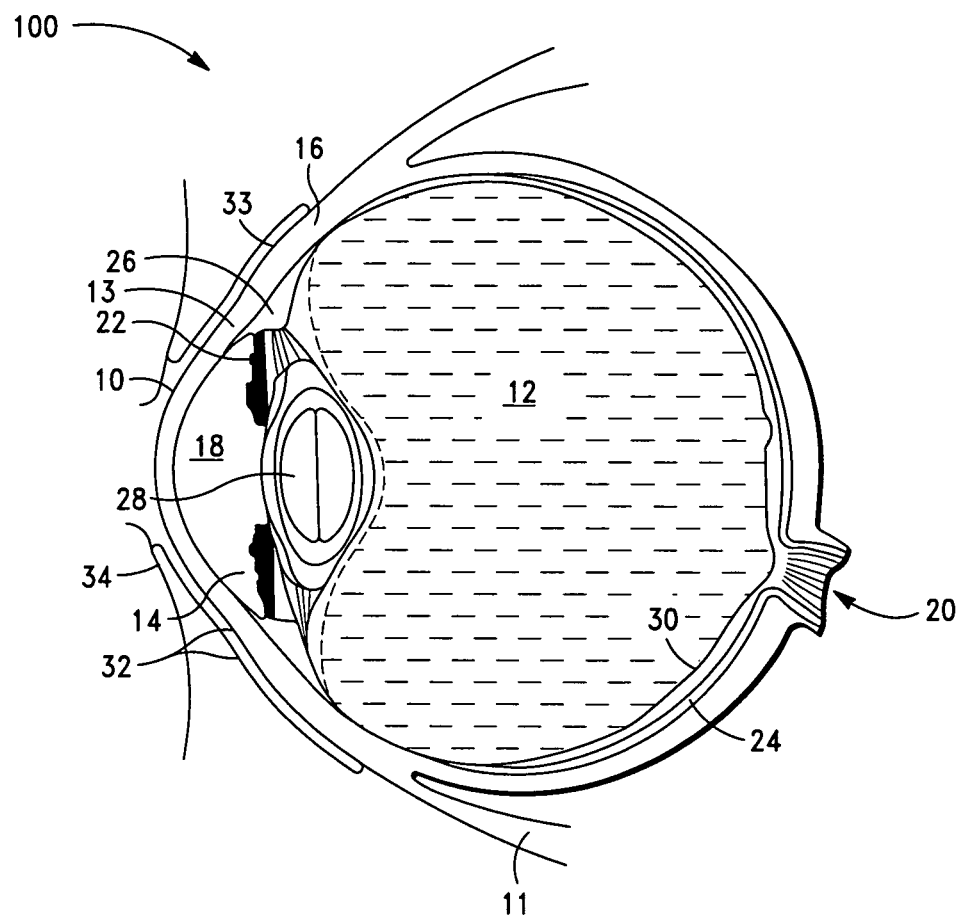
FIG. 1 is a schematic illustration of a human eye.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a," "an," and "the" include plural referents unless the content clearly dictates otherwise. Thus, for example, reference to "pharmacological agents" includes two or more such agents and the like.

DEFINITIONS

The terms "subconjunctival compartment" and "subconjunctival space", as used herein, mean and include the space disposed proximate and under the conjunctiva.

The terms "therapeutic agent," "pharmacological agent," "pharmaceutical agent," "active agent," "agent," and "pharmaceutical composition" are used interchangeably herein and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds.

According to the invention, suitable agents can be selected from, for example, small molecules, such as steroids and NSAIDs, proteins, enzymes, hormones, oligonucleotides, polynucleotides, nucleoproteins, modified DNA and RNA loaded viruses with modified capsid, polysaccharides, glycoproteins, lipoproteins, polypeptides, including drug carriers, such as polymers, micro and nano particles.

Further examples of agents useful in this invention include, without limitation, atropine, tropicamide, dexamethasone, dexamethasone phosphate, betamethasone, betamethasone phosphate, prednisolone, clobetasone, fluorometholone, hydrocortisone, rimexolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, indometacin, ibuprofen, bupivacaine, ropivacaine, dibucaine, etidocaine, tetracaine, lidocaine, xylocalne, procaine, chloroprocaine, prilocalne, mepivacaine, oxybuprocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, nystatin, amphotericin, natamycin, flucytosine, clotrimazole, fluconazole, terbinafine, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, pindolol, and other beta-blocking agents, 6-hydroxydopamine, betaxolol, pilocarpine, carbachol, physostigmine, demecarium, dorzolamide, brinzolamide, adrenaline, dipifevrin, brimonidine, apraclonidine, latanoprost, bimatoprost, travoprost, doconasoids, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF, IGF-2, antibiotics or antifungal drugs, anti pain medication, anesthetics, and combinations thereof, and salts thereof.

The active agent can also be pegylated to enhance the agent's biocompatibility and/or the agent's residence time in the subconjunctival compartment.

It is to be understood that more than one agent can be combined or mixed together and incorporated into or used by the present invention, and that the use of the terms "pharmacological agent," "pharmaceutical agent," "agent," "active agent," and/or "pharmaceutical composition" in no way excludes the use of two or more such "pharmacological agents," "pharmaceutical agents," "agents," "active agents," and "pharmaceutical compositions."

The terms "active agent formulation," "pharmacological agent formulation" and "formulation", as used herein, mean and include an active agent optionally in combination with one or more pharmaceutically acceptable carriers and/or additional inert ingredients. According to the invention, the formulation can be either in solution or in suspension (such as nanoparticles, microspheres or liposomes) in the carrier.

The terms "active agent formulation," "pharmacological agent formulation" and "formulation" also mean and include an active agent that is formulated as an immediate release or a delayed release or a slow release formulation.

The terms "active agent formulation," "pharmacological agent formulation" and "formulation" further mean and include an active agent optionally in combination with one or more viscosity-enhancing materials that are adapted to increase the agent's residence time in the subconjunctival compartment and/or improve the agent's biocompatibility.

In one aspect of the invention, the viscosity-enhancing material comprises a cellulose derivative.

In a further aspect of the invention, the viscosity-enhancing material comprises a polymeric material that is selected from the group consisting of hydroxyethylcellulose (HEC), hydroxypropylmethylcellulose (HPMC), hydroxypropylcellulose (HPC), methylcellulose (MC), hydroxyethylmethylcellulose (NEMC), ethylhydroxyethylcellulose (EHEC), carboxymethylcellulose (CMC), poly(vinyl alcohol), poly (ethylene oxide), poly(2-hydroxyethylmethacrylate), poly(n-vinylpyrolidone), and mixtures thereof.

As used in this application, the term distal designates the end or direction toward the front of a jet injector. The term proximal shall designate the end or direction toward the rear of a jet injector.

As set for the above, the present invention is directed to novel agent delivery apparatus, systems and their methods of use. The invention also provides improved means of performing subconjunctival agent delivery with the benefits of improved safety for the patient and increased efficiency for the practitioner.

The following is a brief description of the key anatomical components of the eye, which will help in the understanding of the various features of the invention:

Referring to FIG. 1, the cornea 10 is the transparent window that covers the front of the eye 100. The cornea 10 is a lens-like structure that provides two-thirds of the focusing power of the eye 100.

The cornea 10 is slightly oval and has an average diameter of about 12 mm horizontally and 11 mm vertically. The central thickness of the cornea 10 is approximately 0.5 mm and approximately 1 mm thick at the periphery.

The sclera 16 is the white region of the eye 100, i.e. posterior five sixths of the globe. The sclera 16 is the tough, avascular, outer fibrous layer of the eye that forms a protective envelope. The sclera 16 is mostly composed of dense collagen fibrils that are irregular in size and arrangement (as opposed to the cornea).

The sclera 16 can be subdivided into three (3) layers: the episclera, sclera proper and lamina fusca. The episclera is the most external layer. The episclera is a loose connective tissue adjacent to the periorbital fat and is well vascularized.

The sclera proper, also called tenon's capsule, is the layer that gives the eye its toughness. The sclera proper is avascular and composed of dense type I and III collagen.

The lamina fusca is the inner aspect of the sclera 16. It is located adjacent to the choroid 24 and contains thin collagen fibers and pigment cells.

The pars plana is a discrete area of the sclera 16. This area is a virtually concentric ring that is located between 2 mm and 4 mm away from the cornea 10.

The mean scleral thickness±SD of the pars plana is reported to be approximately 0.53±0.14 mm at the corneo-scleral limbus, significantly decreasing to 0.39±0.17 mm near the equator, and increasing to 0.9 to 1.0 mm near the optic nerve. At the location of the pars plana, the thickness of the sclera is about 0.47±0.13 mm.

The thickness of the sclera 16 is known to vary according to sex, age, and is altered in various pathological conditions. Overall, the range of thickness of the sclera 16 at the location of the pars plana is estimated to be in the range of approximately 0.3-1.0 mm. The total thickness of the membranes enclosing the eye cavity, at the location of the pars plana, is estimated to be in the range of approximately 0.5-1 mm.

The limbus 13 is the 1-2 mm transition zone between the cornea 10 and the sclera 16. This region contains the outflow apparatus of the aqueous humor 14.

As illustrated in FIG. 1, the extraocular muscles 11 insert into the sclera 16 behind the limbus 13.

The conjunctiva 32 is a thin clear vascular mucous membrane that starts at the limbus 13 and covers the sclera 16 and the inner surface of the eyelid 34. The conjunctiva 32 is composed of layers of non-keratinized stratified columnar epithelium.

The conjunctiva 32 generally comprises three (3) sections: (i) the palpebral conjunctiva, which covers the posterior surface of the eyelids, (ii) the bulbar conjunctiva, which coats the anterior portion of the eyeball, and (iii) the formix, which comprises the transition portion; forming the junction between the posterior eyelid and the eyeball.

Within the bulbar conjunctiva are "goblet cells," which secrete the mucin. This is an important component of the pre-corneal tear layer that protects and nourishes the cornea 10.

The average thickness of the conjunctiva 32 is about 0.05 mm. Although the palpebral conjunctiva is moderately thick, the bulbar conjunctiva is very thin.

The subconjunctival compartment or space 33 is the space disposed proximate and under the conjunctiva 32.

The uvea refers to the pigmented layer of the eye 100 and is made up of three (3) distinct structures: the iris 22, ciliary body 26, and choroid 24. The iris 22 is the annular skirt of tissue in the anterior chamber that functions as an aperture. The iris root attaches to the ciliary body 26 peripherally. The pupil is the central opening in the iris 22.

The ciliary body 26 is the 6 mm portion of uvea between the iris 22 and choroid 24. The ciliary body 26 is attached to the sclera 16 at the scleral spur. It is composed of two zones: the anterior 2 mm pars plicata, which contains the ciliary muscle, vessels, and processes, and the posterior 4 mm pars plana.

The ciliary muscle controls accommodation (focusing) of the lens 28, while the ciliary processes suspend the lens (from small fibers called zonules) and produce the aqueous humor (the fluid that fills the anterior and posterior chambers and maintains intraocular pressure).

The choroid 24 is the tissue disposed between the sclera 16 and retina 30. The choroid 24 is attached to the sclera 16 at the optic nerve 20 and scleral spur. This highly vascular tissue supplies nutrients to the retinal pigment epithelium (RPE) and outer retinal layers.

The layers of the choroid 24 (from inner to outer) are: Bruch's membrane, choriocapillaris, and stroma. Bruch's membrane separates the RPE from the choroid 24 and is a permeable layer composed of the basement membrane of each, with collagen and elastic tissues in the middle.

A suprachoroidal space exists between the choroid 24 and sclera 16. In certain disease processes, fluid or blood can fill this space creating a choroidal detachment.

The crystalline lens 28, located between the posterior chamber and the vitreous cavity, separates the anterior and posterior segments of the eye 100. Zonular fibers suspend the lens 28 from the ciliary body 26 and enable the ciliary muscle to focus the lens 28 by changing its shape.

The retina 30 is the delicate transparent light sensing inner layer of the eye 100. The retina faces the vitreous 12 and consists of two (2) basic layers: the neural retina and retinal pigment epithelium. The neural retina is the inner layer. It has nine (9) layers, including the photoreceptor layer. The retinal pigment epithelium is the outer layer that rests on Bruch's membrane and choroid.

The vitreous humor or vitreous 12 is the largest chamber of the eye (i.e. ~4.5 ml). The vitreous 12 is a viscous transparent gel composed mostly of water. The vitreous 12 also contains a random network of thin collagen fibers, mucopolysaccharides, and hyaluronic acid.

The vitreous 12 adheres firmly to the margin of the optic disc and to the peripheral retina at the ora serrata and the pars plana. With aging, the vitreous 12 liquefies, a process known as syneresis.

The aqueous humor 14 occupies the anterior chamber 18 of the eye 100. The aqueous humor 14 has a volume of about 0.6 mL and provides nutrients to the cornea 10 and lens 28. The aqueous humor 14 also maintains normal IOP.

As will readily be appreciated by one having ordinary skill in the art, the present invention provides improved means of performing subconjunctival agent delivery with the benefits of improved safety for the patient and increased efficiency for the practitioner. The agent delivery apparatus, in accordance with the present invention, is adapted to deliver therapeutic agents, such as liquid agent formulations, to the subconjunctival compartment of patient's eye by delivering very fine streams of the agent formulations at high velocity.

According to the invention, the agent formulations can comprise various forms, including, without limitation, solutions and suspensions.

The invention is also directed to an subconjunctival agent delivery assembly or kit, which, in one embodiment of the invention, includes (1) a pharmacological agent formulation containing an effective amount of an agent useful for treating a condition of a patient's eye; and (2) injector means that is adapted to contain the pharmacological agent formulation and includes force generating means that is adapted to generate sufficient force to expel the pharmacological agent formulation from the injector means into and through the conjunctiva. As indicated above, the pharmacological agent formulation can comprise of various forms, such as a solution or suspension.

In one embodiment of the invention, the injector means provides an injection pressure in the range of approximately 100-1000 psi.

In one embodiment of the invention, the volume of the pharmacological agent formulation delivered to the subconjunctival space is preferably in the range of approximately 0.025-1 mL.

According to the invention, the injector means can comprise a needleless jet injector or a microneedle jet injector, as shown and described in Applicants' U.S. Pat. No. 7,678,078 (hereinafter "the '078 patent); which is expressly incorporated herein in its entirety.

Referring now to FIGS. 2A-2C, there is shown one embodiment of a transfer mechanism 220 of a microneedle jet injector 200 that is disclosed in the '078 patent. As illustrated in FIG. 2B, the transfer mechanism 220 includes a nozzle member 222 having an internal formulation chamber 221 that is adapted to receive a pharmacological agent formulation therein. The nozzle member 222 further includes an opening (or lumen) 223 at the distal end that is in communication with the formulation chamber 221 and is adapted to receive a fixed tubular insert or hollow microneedle 224.

As set forth in the '078 patent, the microneedle 224 can have a penetrating length in the range of approximately 0.1-1 mm. The term "penetrating length" length refers to the actual length of the microneedle 224 that is allowed to penetrate the eye tissue. However, as will be readily appreciated by one having ordinary skill in the art, the length of the microneedle can be readily modified, e.g., diameter, length, etc., to accommodate the subconjunctival delivery methods of the invention.

Referring now to FIG. 2C, the transfer mechanism 220 is designed and adapted to be coupled to a jet injector 200. In the illustrated embodiment, coupling of the transfer mechanism 220 and jet injector 200 is achieved by providing external threads 227 on the end of the nozzle member 222 (see FIG. 1A) that are adapted to cooperate with corresponding threads formed on the inner wall surface of the injector body 202.

In a preferred embodiment of the invention, a needleless jet injector is employed to deliver a pharmacological agent formulation to the subconjunctival space. In one embodiment of the invention, the needleless jet injector preferably includes all of the components and features of the microneedle jet injector described in the '078 patent and shown in FIGS. 2A-2C, with the exception of an injector nozzle substituted for the microneedle.

Figure 3:
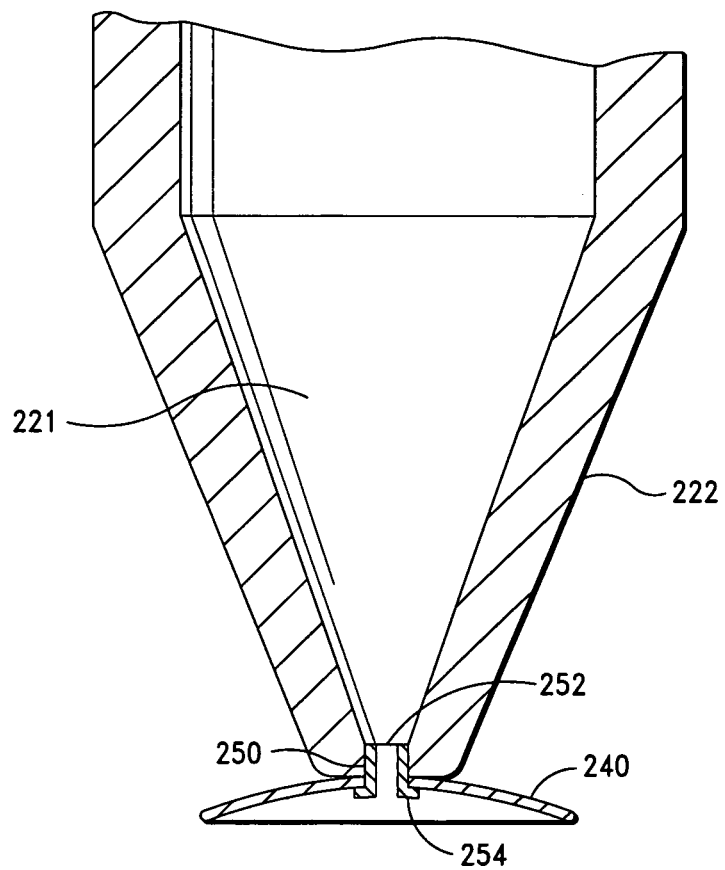
FIG. 3 is a partial sectional front plane view of a needleless jet injector transfer mechanism, in accordance with one embodiment of the invention.

Referring now to FIG. 3, there is shown one embodiment of a needleless jet injector nozzle member 222 having an injector nozzle 250 associated therewith. As illustrated in FIG. 3, the nozzle member 250 includes an internal lumen 252, which is in communication with the internal formulation chamber 221, and flanged end 254.

Preferably, the internal lumen 252 has an internal diameter in the range of approximately 0.025 mm to 0.25 mm.

The injection nozzle may also include an outlet valve member as disclosed in the '078 patent.

According to the invention, the jet injectors of the invention are preferably reusable and can be powered by compressed gas, pyrotechnics, electricity, or a spring, such as disclosed in U.S. Pat. Nos. 5,954,689, 5,704,911, 5,505,697, 6,585,685 and 7,150,409; which are incorporated by reference herein. In all cases, activation of the jet injector 200 is preferably accomplished by depressing an actuation button 201, which triggers the appropriate power source of the jet injector 200.

In an alternative embodiment of the invention, the jet injectors of the invention are disposable, as described, for example in U.S. Pat. No. 6,682,504; which is also incorporated by reference herein. The jet injectors can also be preassembled and ready for use without any further assembly.

As is well known in the art, use of a conventional jet injector is, however, technically challenging. If the jet injector is not positioned perpendicular to the tissue interface or if a poor contact is established between the nozzle and the tissue at the time of injection, a "wet" injection may occur. A wet injection is characterized by loss of a significant fraction of the medication at the surface of the tissue and/or, in the case of the skin, injection of the medication into the dermis instead of the subcutaneous or intramuscular space.

One of the root causes for wet injection is non-perpendicularity of the nozzle with the surface of the tissue, which results in the jet contacting the surface of the tissue at an angle. This can result in reflection of all or part of the jet by the tissue surface and/or total or partial intradermal injection.

Another cause for wet injection is poor contact with the tissue, which results in dissipation of a significant fraction of the jet energy through air aspiration that may be injected concomitantly with the medication.

Although wet injection is not desirable during transdermal administration, its consequences are relatively benign and a small percentage of such failure is generally deemed acceptable.

In the case of subconjunctival agent delivery, wet injection would result in significant loss of the pharmacological agent formulation or medication at the surface of the conjunctiva, which could likely cause potential harmful consequences depending of the agent being delivered. Additional potential adverse consequences include air/contamination entrapment, potentially resulting in tissue damage, infection and subsequent inflammation.

As will thus be readily appreciated by one having ordinary skill in the art, the use of a subconjunctival agent delivery apparatus and/or system having a positioning platform that is adapted to position and secure the apparatus to the eye structure, e.g., conjunctiva, or tissue prior to dispensing a pharmacological agent formulation, minimizes the risk of wet injection. Thus, in a preferred embodiment of the invention, the injector means include a positioning platform 240 (see FIGS. 1B and 2) to ensure desired positioning, e.g., perpendicularity, and anchoring of the agent delivery apparatus to a surface of an eye structure, e.g. conjunctiva, thereby minimizing air entrapment and bacterial contamination.

According to the invention, the platform 240 can comprise various shapes, e.g., circular, kidney shaped, star shaped, etc. In the illustrated embodiment, the platform 240 has a substantially circular shape.

As is well known in the art, needleless delivery of a pharmacological agent formulation to the eye typically requires a delivery pressure greater than approximately 4000 psi (measured as the force of the fluid stream divided by the cross-sectional area of the fluid stream) to penetrate all of the layers of the eye.

Applicants have, however, found that a delivery pressure of only approximately 100 to 1000 psi is required to effectuate pharmacological agent transfer through the conjunctiva with a needleless agent delivery apparatus of the invention. Applicants further submit that the noted delivery pressure range offers the greatest safety for subconjunctival agent delivery.

The noted pressure range is, however, dependent on a number of factors, including the size of the nozzle and the volume of pharmacological agent formulation to be delivered.

Thus, in a preferred embodiment of the invention, the jet injectors are capable of providing an agent delivery pressure in the range of approximately 100-1000 psi.

Figure 4C:
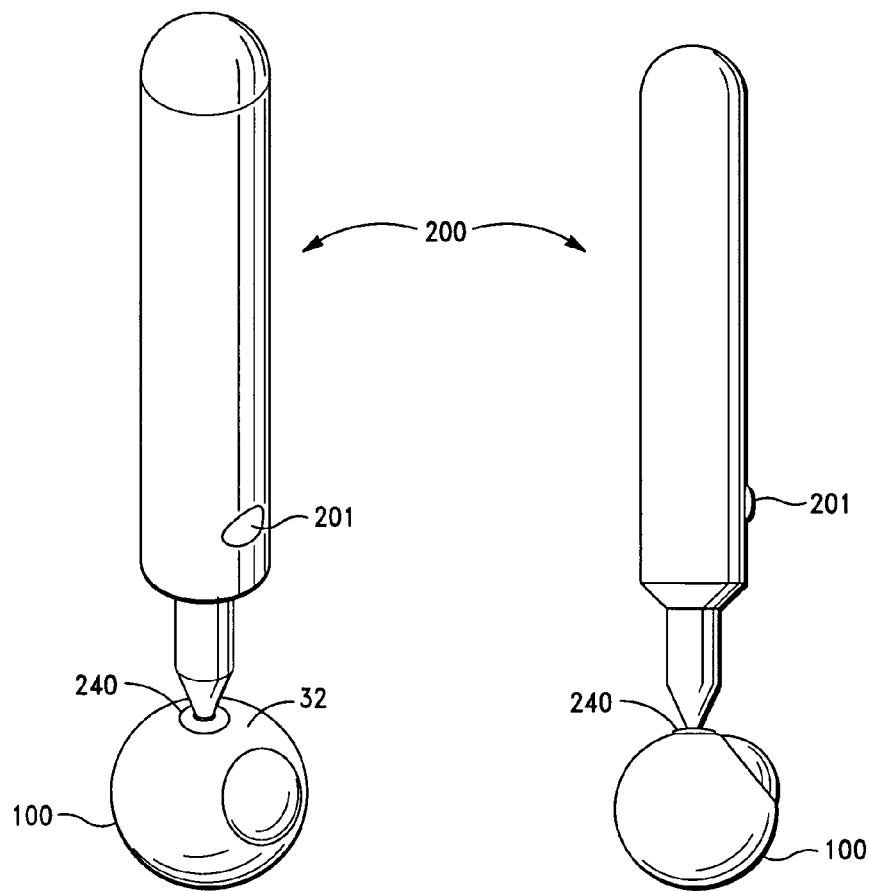
FIG. 4C is a perspective view of the assembled needleless jet injector shown in FIGS. 4A and 4B positioned on the eye, in accordance with one embodiment of the invention.
Figure 4C:
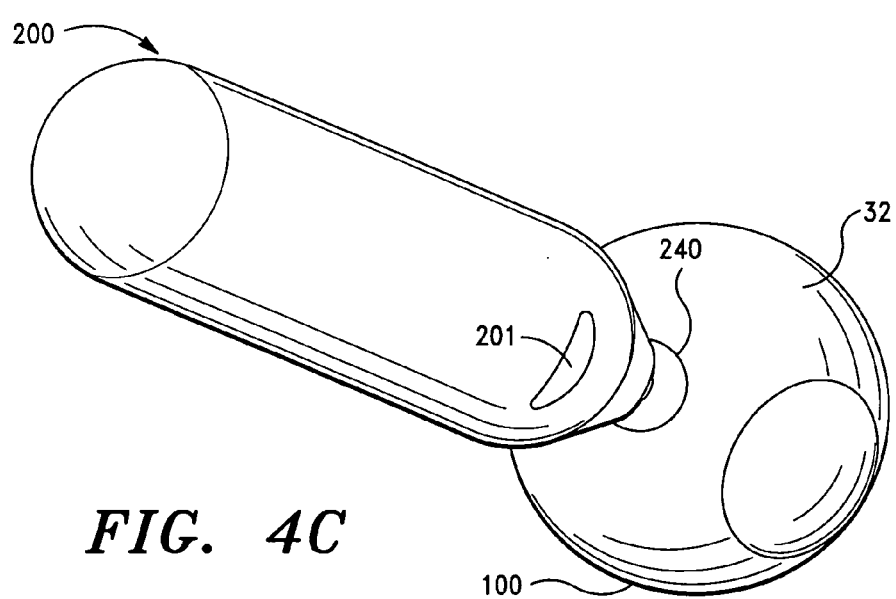

Referring now to FIGS. 4A-4C, there is shown illustrations of a needleless jet injector 200 positioned on an eye 100 to effectuate delivery of a pharmacological agent formulation to the subconjunctival compartment of the eye 100.

According to the invention, the pharmacological agent formulation to be administered can be contained in the internal formulation chamber 221 of the injector 200, or, as set forth in the '078 patent, the pharmacological agent formulation can be contained in a disposable prefilled cartridge that is operatively receivable by the jet injector 200.

As illustrated in FIGS. 4A-4C, in a preferred embodiment of the invention, to administer a pharmacological agent formulation to the subconjunctival compartment of the eye 100, the distal surface of the injector platform 240 is initially positioned on the conjunctiva 32. The activation button 201 is then depressed, whereby the injector 200 is activated and the agent formulation is expelled from the jet injector 200 and delivered to the subconjuntival compartment of the eye 100.

EXAMPLES

The following examples are provided to enable those skilled in the art to more clearly understand and practice the present invention. They should not be considered as limiting the scope of the invention, but merely as being illustrated as representative thereof.

Example 1

The nozzle of a needleless jet injector was equipped with an 8 mm circular platform. The needleless jet injector was filed with a blue dye solution and was equipped with different springs.

Frozen enucleated rabbit eyes were thawed at 4° C. for 6 hours and placed on sterile gauze imbibed with sterile saline for another hour at 4° C. The rabbit eyes were subsequently taken to room temperature and used within the next 2 hours.

Each eye was then injected with a blue dye following positioning of the platform to the conjunctiva of the eye. The injected volume of the dye was 0.1 mL.

Successful needleless delivery was evidenced by the immediate apparition of the blue dye within the vitreous and negligible leakage outside the eye at the time of injection. Criteria for successful subconjunctival injection included absence of dye within the vitreous, immediate apparition of the blue dye in the subconjunctival space and negligible leakage outside the eye at the time of injection.

Table 1 shows the number of deliveries obtained with the different springs listed in order of decreasing delivery pressure (measured as the force of the fluid stream divided by the cross-sectional area of the fluid stream).

Delivery pressures required to achieve subconjunctival delivery comprised between approximately 100 and 1000 psi. Above 1000 psi, intravitreal delivery was observed. Below about 100 psi, wet injections were observed.

TABLE 1

| Spring # | Pressure (psi) | Intravitreal | Number of Deliveries Subconjunctival | Wet |
|---|---|---|---|---|
| 1 | 1083 | 6 | 0 | 0 |
| 2 | 731 | 1 | 5 | 0 |
| 3 | 326 | 0 | 15 | 0 |
| 4 | 174 | 0 | 6 | 0 |
| 5 | 82 | 0 | 0 | 6 |

As will readily be appreciated by one having ordinary skill in the art, the present invention provides numerous advantages compared to prior art methods and systems for administering agents and formulations thereof to subconjunctival compartment of the eye. Among the advantages are the following:

The provision of a subconjunctival agent delivery method and system that provides safe, accurate, consistent, and rapid injection of therapeutic agents into the subconjunctival compartment of the eye.

The provision of a subconjunctival agent delivery method and system that facilitates delivery of therapeutic agents into the subconjunctival compartment of the eye with minimal risk of trauma and infection.

The provision of a subconjunctival agent delivery method and system that facilitates delivery of agents into the subconjunctival, subtenon spaces or intrascleral and subchoroidal space of an eye.

The provision of a subconjunctival agent delivery method and system that provides semi-automated delivery of therapeutic agents into the subconjunctival compartment of the eye.

Without departing from the spirit and scope of this invention, one of ordinary skill can make various changes and modifications to the invention to adapt it to various usages and conditions. As such, these changes and modifications are properly, equitably, and intended to be, within the full scope and range of equivalence of the invention.

What is claimed is:

1. A method for administering a pharmacological agent formulation to a subconjunctival compartment of an eye, comprising the steps of:

providing a subconjunctival agent delivery apparatus containing the pharmacological agent formulation in an internal formulation chamber, said agent delivery apparatus including needleless injector means that is in communication with said internal formulation chamber, said needleless injector means including a first transfer mechanism having an integral nozzle member-guide platform assembly, said nozzle member-guide platform assembly comprising a first nozzle member and a deformable guide platform that is adapted to substantially conform to a first surface of a first eye structure and position said subconjunctival agent delivery apparatus on said eye structure when in an engagement position thereon, and force generating means that is adapted to generate sufficient force to expel the pharmacological agent formulation from said agent delivery apparatus and into and through an eye structure;

positioning said subconjunctival agent delivery apparatus on said first surface of said first eye structure; and activating said subconjunctival agent delivery apparatus, whereby said pharmacological agent formulation is expelled from said subconjunctival agent delivery apparatus and delivered to said first surface of said first eye structure with a delivery pressure in the range of approximately 100-1000 psi and, whereby a first volume of said pharmacological agent formulation is administered to the subconjunctival compartment of the eye.

2. The method of claim 1, wherein said first volume of the pharmacological agent formulation is in the range of approximately 0.025-1 ml.

3. The method of claim 1, wherein said first eye structure comprises the conjunctiva.

4. The method of claim 1, wherein said guide platform further includes suction means that provides an eye engagement force and seals said guide platform to said first eye structure when said guide platform is in said engagement position.

* * * * *